(12) United States Patent
Paakkinen (10) Patent No.: US 6,904,693 B2
(45) Date of Patent: Jun. 14, 2005

(54) METHOD AND DEVICE FOR DEFINING ELASTIC DEFORMATIONS AND INTERNAL ANGLE OF A GYRATORY COMPACTOR

(75) Inventor: Antti Paakkinen, Jyvaskyla (FI)

(73) Assignee: Pine Instrument Company, Grove City, PA (US)

( * ) Notice: Subject to any disclaimer, the term of this patent is extended or adjusted under 35 U.S.C. 154(b) by 0 days.

(21) Appl. No.: 10/394,633

(22) Filed: Mar. 21, 2003

(65) Prior Publication Data

US 2004/0181956 A1 Sep. 23, 2004

(30) Foreign Application Priority Data

Mar. 22, 2002 (FI) .............................................. 20020560
Nov. 15, 2002 (FI) .............................................. 20022035

(51) Int. Cl.$^7$ .............................. G01B 3/56; G01N 3/08
(52) U.S. Cl. .............................. 33/534; 33/542; 33/555; 73/818; 73/824
(58) Field of Search ......................... 33/832, 833, 533, 33/534, 605, 655, 542, 551, 555, DIG. 15; 73/760, 788, 594, 761, 813, 818, 824, 866

(56) References Cited

U.S. PATENT DOCUMENTS

| | | | |
|---|---|---|---|
| 2,972,249 A | | 2/1961 | McRae et al. |
| 3,461,717 A | | 8/1969 | Dunlap et al. |
| 3,478,572 A | | 11/1969 | McRae |
| 4,087,918 A | | 5/1978 | Schmid et al. |
| 4,265,026 A | * | 5/1981 | Meyer .......................... 33/542 |
| 4,794,799 A | | 1/1989 | Paakkinen |

(Continued)

FOREIGN PATENT DOCUMENTS

| | | |
|---|---|---|
| EP | 1 348 942 A2 | 1/2003 |
| WO | WO0186251 | 11/2001 |

OTHER PUBLICATIONS

Test Quip, "Operating Instructions for the Dynamic Angle Validation Kit (DAV) for Superpave Gyratory Compactors", TestQuip Model DAV1, pp. 1–40.

Dalton, Frank, "Gyratory Compaction, The Significance of the Internal Angle of Gyration", pp. 1–45.

"TRB Superpave Mixture & Aggregate Expert Task Group", Apr. 4, 2001, pp. 1–13.

NCAT, "Evaluation of the Superpave Gyratory Compactor's Internal Gyration Angle in Alabama", pp. 1–31.

Pine Instrument, "Investigation of FHWA SGC AVK #3 Guide Rod Play", Sep. 27, 2000, pp. 1–8.

"Pressure Response Indicator HM–855", Last viewed on Oct. 17, 2003, p. 1, Gilson Company, Inc., http://www.globalgilson.com/sections/product/index.asp?pr_id=14171.

(Continued)

*Primary Examiner*—Christopher W. Fulton
*Assistant Examiner*—Madeline Gonzalez
(74) *Attorney, Agent, or Firm*—Roetzel & Andress (57) ABSTRACT

The object of the invention is a method for defining elastic deformations and integral angle between of the most important parts of a gyratory compactor, in which method the angle of gyration of a gyratory compactor is measured during the use of the gyratory compactor. The object of the invention is also a device in accordance with the claim 1, which device includes measuring elements (13, 20, 27, 28) for measuring the angle of gyration of a gyratory compactor. Characteristic to the method in accordance with the invention is the fact that a loading device (1) is adjusted in the place of mass specimen, the loading of which on the gyratory compactor is earlier known and that the gyratory compactor will be in use while the loading device (1) is inside the gyratory compactor. Characteristic to the device in accordance with the invention is the fact that the device includes at least one loading device which can be placed inside the specimen cylinder mold of the gyratory compactor.

15 Claims, 4 Drawing Sheets

U.S. PATENT DOCUMENTS

| | | | |
|---|---|---|---|
| 4,918,825 A | * | 4/1990 | Lesh et al. .................... 33/833 |
| 4,930,346 A | | 6/1990 | Paakkinen et al. |
| 4,942,768 A | | 7/1990 | McRae |
| 5,036,709 A | | 8/1991 | McRae |
| 5,275,056 A | | 1/1994 | Hamilton et al. |
| 5,323,655 A | | 6/1994 | Eagan et al. |
| 5,456,118 A | | 10/1995 | Hines et al. |
| 5,606,133 A | | 2/1997 | Hines et al. |
| 5,698,789 A | | 12/1997 | Lainio et al. |
| 5,817,946 A | | 10/1998 | Brovold |
| 5,824,913 A | | 10/1998 | Pyle |
| 5,911,164 A | | 6/1999 | McRae |
| 5,939,642 A | | 8/1999 | King et al. |
| 6,026,692 A | | 2/2000 | Brovold |
| 6,205,864 B1 | | 3/2001 | Vialletel et al. |
| 6,412,187 B1 | * | 7/2002 | Sasaki et al. .................. 33/542 |
| 6,477,783 B1 | | 11/2002 | Harman et al. |
| 2001/0049969 A1 | | 12/2001 | Bahia et al. |
| 2003/0075820 A1 | * | 4/2003 | Hines ......................... 73/818 |
| 2003/0089178 A1 | | 5/2003 | Paakkinen |
| 2003/0192384 A1 | | 10/2003 | Verna |
| 2004/0020306 A1 | * | 2/2004 | Moscrip et al. ............... 73/824 |

OTHER PUBLICATIONS

Guler, Murat, et al., "Development of a Device for Measuring Shear Resistance of HMA in the Gyratory Compactor", pp. 1–24, Paper No. 00–1318, The Asphalt Research Group.

"Gyratory Asphalt Mixture Design Gyratory Compactor Calibration", Apr. 4, 2001, pp. 1–2.

Raw Data from Recent Field Trials Using the Superpave Gyratory Compactor Dynamic Angle Validator (DAV), prepared for the Superpave ETG Meeting, Tempe, Arizona, Apr. 2–4, 2001.

Report 2001–01 Application of Internal Angle Verification to Obtain Equilavent Results from Various SGC Models, Pine Instrument Company, Aug. 23, 2001, pp. 1–9.

"Report 2000–03 Investigation of Pine Superpave Gyratory Compactors Using the FHWA Angle Validation Kit", Pine Instrument Company, Dec. 29, 2000, pp. 1–9.

"Report 2000–02 Observations of SGC End Plate Deflection Using the FHWA Angle Validation Kit", Pine Instrument Company, Oct. 11, 2000, pp. 1–11.

Al–Khateeb, Ghazi, et al., "Target and Tolerance Study for the Angle of Gyration used in the Superpave Gyratory Compactor (SGC)", http://www.tfhrc.gov/pavement/asphalt/labs/mixtures/targe.htm, Aug. 22, 2002, pp. 1–16.

Superpave Gyratory Validation Kit Manufacturer's Meeting, 08/31, pp. 1–7.

"Consideration of Mold Temperature When Measuring the Angle of Gyration on the Troxler Model 4140", Oct. 2001, pp. 1–6.

"Measuring the Angle of Gyration on the Troxler Superpave Gyratory Compactor—SGC Using an Internal Angle Measuring Device", pp. 1–4.

"Troxler's Superpave Gyratory Compactor Operational Specifications", Feb. 2001, pp. 1–5.

"Investigating Measurable Gmb Differences Among Gyratory Compacted Specimens", May 2001, pp. 1–9.

"FGWA Angle Kit Studies at Pine", pp. 1–14.

"Economic Impact Refining the Dynamic Internal Angle of the Superpave Gyratory Compactor", Jan. 29, 2003, pp. 1–10.

Buchanan, Shane, M., et al., "Effect of Superpave Gyratory Compactor Type on Compacted Hot Mix Asphalt (HMA) Density", Jan. 7–11, 2001, pp. 1–23.

Pine Instrument Company, Report 2000–01, "Superpave Gyratory Compactors—Angle Sensitivity", Mar. 30, 2000, pp. 1–9.

Schiebel, Bill, "CDOT and Colorado Paving Industry's Action Plan to Address Recently Documented Issue with Compaction Angle . . . ", Apr. 19, 2002, pp. 1–16.

"Model 3191 True Mold Angle Device for the Model 4141 Gyratory Compactor", pp. 1–16.

"Model 3190 True Mold Angle Device for the Model 4140 Gyratory Compactor", pp. 1–20.

* cited by examiner

METHOD AND DEVICE FOR DEFINING ELASTIC DEFORMATIONS AND INTERNAL ANGLE OF A GYRATORY COMPACTOR

CROSS REFERENCE TO RELATED APPLICATIONS

This application claims the benefit of Patent Application No. FI-20020560, filed in Finland on Mar. 22, 2002. This application claims the benefit of Patent Application No. FI-20022035, filed in Finland on Nov. 15, 2002.

FIELD OF THE INVENTION

The present invention relates to a method for accurately inducing elastic deformations of a gyratory compactor, and measuring the internal angle of gyration. The internal angle of gyration is the angle formed between the axis of a cylindrical mold and the end plates of the mold.

BACKGROUND OF THE INVENTION

A gyratory compactor is used for defining properties of compaction of various masses of soil and similar substances, such as bituminous asphalt. For measurements the specimen mold of a gyratory compactor is filled with mass specimen. The specimen is compressed under vertical pressure and the so called gyratory movement, which causes shear strain across the specimen. These actions make the particles of the specimen to move in respect with each other finding their positions tighter to each other, compacting the mass specimen and leading to increasing density. At the same time the gyratory compactor frame is experiencing forces due to deformation resistance of the specimen. These forces are greater where the pressure and cross-sectional deformation due to it are greatest. In a gyratory compactor this point is on the direction where the angle of gyration of gyratory motion is turning. Due to this force, the gyratory compactor frame bends (like a stiff spring) usually such that the angle of gyration (gyratory angle) tends to decrease. As the compaction test continues the density and usually also the shear resistance increase. Due to this force, the elastic deformation of the compactor and the decrease of the internal angle of gyration are at minimum in the beginning of the test and at maximum usually at the end of the test.

A change in the angle of gyration is usually the most significant factor of error having influence on results in measuring compaction properties in gyratory compactor. In some present gyratory compactors the angle of gyration in the end of a test may be more than 10% smaller than in the beginning of the test. The compaction results of tests carried out with these kinds of gyratory compactors are examined, however, assuming that the angle of gyration has remained equal during the whole length of the test. Therefore, many different models of gyratory compactors at present give deviating results to each other in measuring compaction properties. The situation is especially serious when the mass specimen is causing heavier loadings or variable loadings to the gyratory compactor (i.e. a "stiff" or coarse mixture).

According to present standards, correlation between the angle of gyration of gyratory compactors is defined by measuring the compacted density of hot mix mass specimens from the same source with different gyratory compactors. This aims to clarify differences between gyratory compactors by comparing test results of different gyratory compactors. Sometimes based on these differences the elastic properties of different gyratory compactors as well as other quality factors are tried to be determined. This kind of studying of tests and their results is rather troublesome and slow. Furthermore, measuring results gathered with this kind of method are inaccurate, among other things, because properties and density of mass specimen vary uncontrollably and relatively much, although the mass specimen has been taken from the same mass specimen source.

An angle measurement device which can be put into a specimen mold of a gyratory compactor is known from the patent U.S. Pat. No. 6,477,783. The device is placed inside a cylinder mold in the bottom or top against the bottom or top piston along with the asphalt mixture. There is a fixed and a movable probe tip against the mold wall, which are placed vertically in a distance from one another. The measuring result from the movable probe tip in relation to the position of the fixed probe tip is in proportion to the angle of gyration of the gyratory compactor. To measure the effective angle of gyration of a gyratory compactor, the device and a hot mix mass specimen is placed in the specimen mold with the hot mix placed above or under the measuring device. The gyratory compactor is then operated in a way corresponding to the normal compacting of mass specimen. From the position between the movable probe tip and the fixed probe tip the angle of gyration of the gyratory compactor is defined during the compaction of mass specimen in the specimen cylinder mold.

There are many disadvantages and imperfections connected to the measuring device of U.S. Pat. No. 6,477,783. Firstly, the measuring device takes part of the space meant for a mass specimen, so that a mass specimen smaller than normal must be used or the compaction pistons are further away from each other than during normal compaction. Therefore angle measurements taken do not correspond to the actual compacting situation of a mass specimen. When the measuring device is shorter in order to decrease the above mentioned disadvantages, the probe tips must be adjusted closer to each other on the vertical axis, which creates more inaccuracy in measuring. Furthermore, the magnitude of loading from a mass specimen to the gyratory compactor is unknown beforehand, and the mass specimen to be placed above or under the measuring device is different by density properties every time when measured, because every time the measurement is made there must be a new mass specimen in the specimen cylinder mold. Therefore, while using the device presented in the patent above several rather long individual test measurements must be carried out if elastic deformations of a gyratory compactor is wanted to define reliably and exactly enough. Furthermore, due to its construction the measuring device is exposed to heat damage while using hot asphalt specimens. Also impurities may stick to probe tips affecting the measuring accuracy. These all are additional to elements of uncertainty in use of the measuring device as well as difficulties in measuring process presented in patent above.

SUMMARY OF THE PRESENT INVENTION

The purpose of this invention is to provide a method and a device, which reduces or eliminates earlier mentioned problems connected with present methods of defining elastic deformations and internal angles of gyratory compactors. Especially, the purpose of the invention is to provide a method and a device, by use of which the elastic properties of a gyratory compactor frame can be defined. Further by using the method and device, important factors expressing the quality of a gyratory compactor depending on elastic properties are easily and reliably defined. Furthermore, the purpose of the invention is to provide a method, which is quick and easy to use as well as a device, which is accurate and reliable but simple and advantageous by construction.

Characteristic to the method in accordance with the invention is the fact that a mass specimen is replaced with a load generating device (loading device), where the load level on the gyratory compactor is known, and that the gyratory compactor is used while the load generating device is inside the mold in the gyratory compactor. Using this load generating device where the load level on the gyratory compactor is known, instead of a mass specimen when defining elastic properties and integral angle, errors due to changes in stiffness and density of a mass specimen are eliminated. Furthermore, the beforehand known loading caused by the load generating device may easily be changed to another known value in order to find out reliably and exactly the correlation between elastic deformations of a gyratory compactor and the magnitude of load.

In an advantageous application of the method in accordance with the invention, at least two measurements of the angle of gyration of a gyratory compactor are carried out with different generated load values. This way it is possible to find out the influence of the change in load on elastic deformations of a gyratory compactor and the magnitude of elastic deformation as a function of load can be defined. By means of connection between the load and elastic deformation achieved this way it is possible to understand the meaning of elastic deformations caused by various masses and their influence on compaction properties to be defined.

In the second advantageous application of the method correlation between the angle of gyration and the load may be taken into account in calculations of density properties after measurements such that the actual angle of gyration defined based on elastic deformations is used in calculations. This improves the reliability and accuracy of the results of the experiment on gyratory compaction.

In the third advantageous application of the method in accordance with the invention, the load from the load generating device is changed by changing at least one of the contact points of the load generating device and the gyratory compactor. The change of the contact point may be carried out between two measurements of defining the elastic deformation simply, easy and quickly. Furthermore, the value of various loads created by changing the contact point may be defined by simple calculations very accurate when the pressing force on the cover and bottom of the specimen cylinder mold is known.

In the fourth advantageous application of the method in accordance with the invention the contact points between the load generating device and the gyratory compactor are changed by mounting at least one additional part changing the contact points of the load generating device. This way changing the contact points may be carried out easy, quickly and accurately repeatable.

In the fifth advantageous application of the method in accordance with the invention, the angle of gyration of the gyratory compactor is measured with a length dial gauge. The dial gauge may be placed inside a standard size specimen cylinder mold easy and fixed to a suitable place with a simple fixing construction such that the tip of the dial gauge measures the angle between the cover or bottom of the specimen cylinder mold and the sidewall of specimen cylinder mold such that the angle of gyration may be defined with simple calculations from that result. Furthermore, results from the dial gauge may relatively easy be either collected to the memory of the device or transmitted to a processing unit for measuring results in real-time outside the gyratory compactor.

In the sixth advantageous application of the method in accordance with the invention, the angle of gyration of a gyratory compactor is measured by means of optical measuring elements mounted in the specimen cylinder mold. This way the measuring of the angle of gyration may be carried out extremely accurately, because in these kind of measurements the changes in elastic deformations may be examined while optically magnified. Furthermore, the transfer of measuring information by means of optical measuring elements outside the specimen cylinder mold may be carried out simply and advantageously by reflecting the light beam describing the changes due to elastic deformations through an opening in the specimen cylinder mold outside the gyratory compactor.

Characteristic to a device in accordance with invention is the fact that the device includes at least one load generating device to be placed inside the specimen cylinder mold of a gyratory compactor. While using the method in accordance with the invention it is possible by means of a load generating device to expose to the gyratory compactor such load corresponding the load of the mass specimen, very easy and simply, and so defining the elastic deformations of the gyratory compactor by measuring the value of the angle of gyration. This may be carried out reliably and exactly without troublesome and slow comparing measurements or use of hot mix as in present methods.

In an advantageous application of the device in accordance with the invention there is a cylindrical part, which can be placed inside the specimen cylinder mold moving with minimal clearance. This kind of part is suitable and easy to be placed inside a specimen cylinder mold of most present known gyratory compactors and this kind of part may be made to cause loads closely resembling mass specimen while pressed between the cover and the bottom of a specimen cylinder mold in a gyratory compactor. Furthermore, in this kind of cylindrical part it is easy to install measuring devices/device with which it is possible to measure the actual internal angle of gyration of a gyratory compactor during the use of a gyratory compactor. Furthermore, the character and the magnitude of loads from this kind of load generating device may easily be changed to resemble the changes caused by density and stiffness of the mass specimen by changing the contact points between the cover and the bottom and the load generating device.

In the second advantageous application of the device in accordance with the invention, the load generating device includes at least one additional part which can be mounted to the load generating device in order to change the magnitude of loads caused by the load generating device to the gyratory compactor. By using additional parts it is possible to change contact points between the loading device and the bottom and the cover. In that way loads caused by the loading device to the specimen cylinder mold, cover and bottom are similar to the changes caused by the changes of properties of mass specimen. Also, the magnitude of the load is easy to be defined by calculations from pressing forces against the bottom and the cover. Due to this it is possible by means of this kind of equipment to define the correlation between elastic deformations of a gyratory compactor and the magnitude of the load of mass specimen reliably and exactly.

Next, the invention will be explained in more detail with reference to the accompanying drawings, in which,

DETAILED DESCRIPTION OF PREFERRED AND ALTERNATE EMBODIMENTS

A device of the invention includes a loading device suitable to be placed into a specimen cylinder mold of a gyratory compactor as well as measuring elements for measuring the angle of gyration and a processing unit for measuring results to be connected to measuring elements for processing the measuring results of the angle of gyration and converting to elastic deformations of a gyratory compactor.

Figure 1:
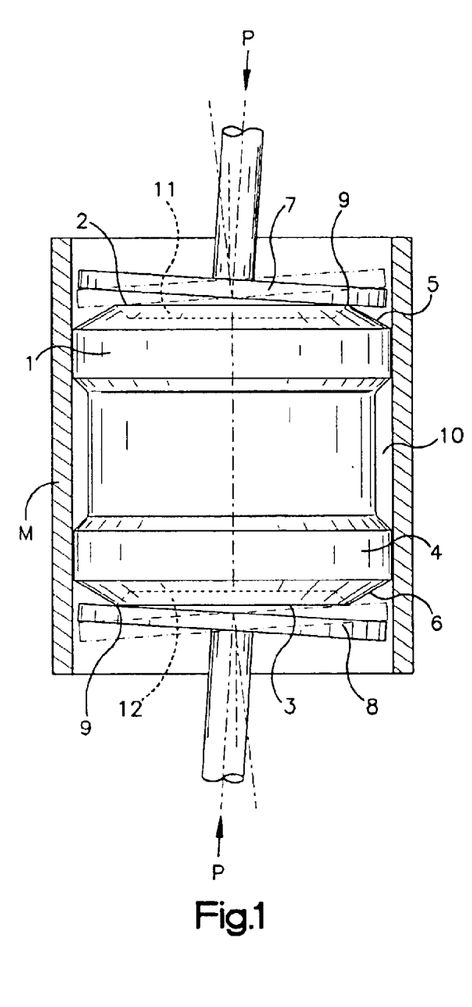
FIG. 1 illustrates a vertical cross-section of a specimen cylinder mold with a loading device of the invention placed in it.

In FIG. 1 there is a loading device 1 placed into a specimen cylinder mold M of a gyratory compactor. The loading device in accordance with FIG. 1 has been made of suitable solid material, such as steel, aluminum or plastic, with a body in the shape of a cylinder with head surfaces 2 and 3, as well as casing surface 4 between the head surfaces. The head surfaces 2 and 3 extend or project from respective ends of the loading device body. The diameter of the loading device is such that it can be placed inside a standard size specimen cylinder mold of a gyratory compactor with close clearance but easy to move inside the cylinder mold. There are chamfers 5 and 6 on the edge of the head surfaces of the loading device so that the cover 7 and the bottom 8 of the specimen cylinder mold make contact with the loading device controlled at the contact points 9 on the head surfaces 2 and 3. These contact points remain for the whole time of use of the gyratory compactor at constant distance from the central axis of the loading device. Due to this, the load on the gyratory compactor may be defined by calculating, using the pressing force P affecting the cover and the bottom. The loading device includes as well a groove 10 made to the central area of the casing surface. The meaning of it is to prevent the contact between the casing surface with the specimen cylinder mold at the central area of the loading device, such that defining of loads between the loading device and the specimen cylinder mold would be as exact and easy as possible. There are hollows 11 and 12 on the head surfaces 2 and 3. The shape and depth of them allows to adjust ring like additional parts (not included in FIG. 1) being parts of the device, with which the loads caused by the loading device to the gyratory compactor are changed (in FIG. 1 bending moments formed in the bottom and in the cover). Head surfaces 2 and 3 can be formed integrally with the body, or attached to or otherwise fixedly positioned at the respective ends of the loading device body.

Figure 2:
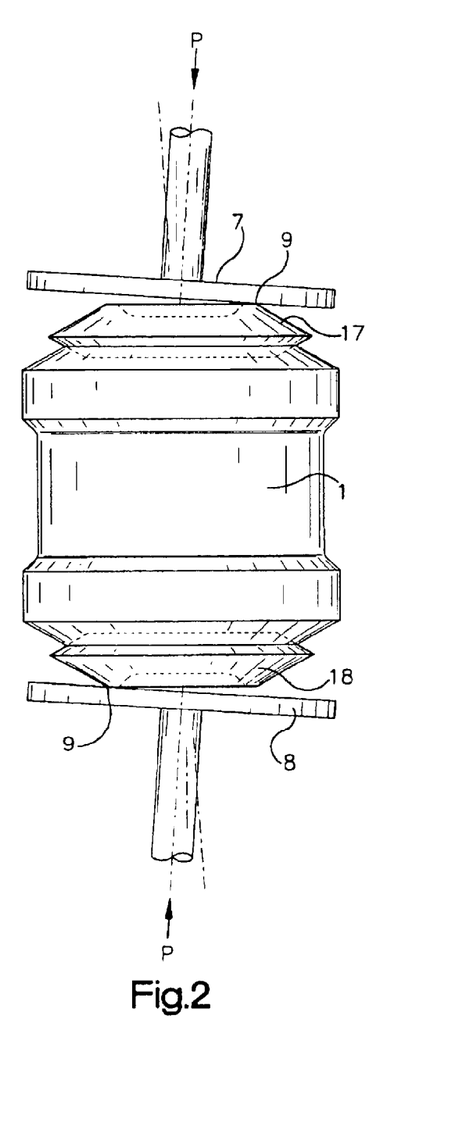
FIG. 2 illustrates a loading device in accordance with FIG. 1 between the cover and the bottom of a specimen cylinder mold from side, with additional parts changing the magnitude of load.

The additional parts in the loading device in accordance with FIG. 1 are ring like parts made such that they reach from the bottom of hollows 11 and 12 outside the head surfaces 2 and 3 on vertical axis. FIG. 2 illustrates, as an example of these kinds of additional parts, 17 and 18 added to a loading device in accordance with FIG. 1. While the loading device is inside the specimen cylinder mold and the additional parts 17 and 18 are placed in the loading device, the cover 7 and bottom 8 the of the specimen cylinder mold are in contact only with the additional parts 17 and 18 at the contact points 9'. While comparing FIGS. 1 and 2 one can see that the additional parts 17 and 18 added to the loading device causes the contact point between the cover 7 and the bottom 8 and the loading device to change in extent of the radius of the loading device. The additional parts 17 and 18 are placed inside the hollows 11 and 12 suitably without clearance while mounted in the loading device. Therefore the contact point of the cover 7 and the bottom 8 of the specimen cylinder mold and the additional parts stay always in a constant distance from the vertical center line of the loading device. Therefore the bending moments due to the loading device will remain constant considering that the force P on the cover and the bottom is not changed. Therefore the bending moments due to the loading device may be exactly and reliably defined beforehand also where the additional parts 17 and 18 are used in the loading device. In an alternate embodiment of the loading device 1, the hollows 11 and 12 are not required, and the additional parts 17 and 18 are mechanically fastened or otherwise positioned on the ends of the loading device body.

As earlier mentioned the contact points of the cover and the bottom to the loading device change when the additional parts 17 and 18 are placed between the cover 7 and the bottom 8 and the loading device 1. Due to change in contact points the bending moments to the cover and the bottom from the loading device change. Therefore by changing the diameter and the shape of the additional parts the magnitude of the bending moment to the bottom and the cover may be changed and are exactly repeatable. Therefore by means of additional parts causing a different contact point it is possible to simulate various mass specimens and influences of compaction of mass specimen on loads of gyratory compactor during the compaction test. In case the contact point of the cover and the bottom and the loading device are placed in such distance from the vertical center line of the loading device that is, for example, 20% of the radius of the loading device the bending moment will equal to that of a certain mass specimen in the beginning of the test. Correspondingly, for example, in the end part of the compaction test of said mass specimen the bending moment due to more dense mass grows such that the corresponding contact point may locate in such a distance from the vertical center line of the loading device that is 40% of the radius of the loading device.

Figure 3:
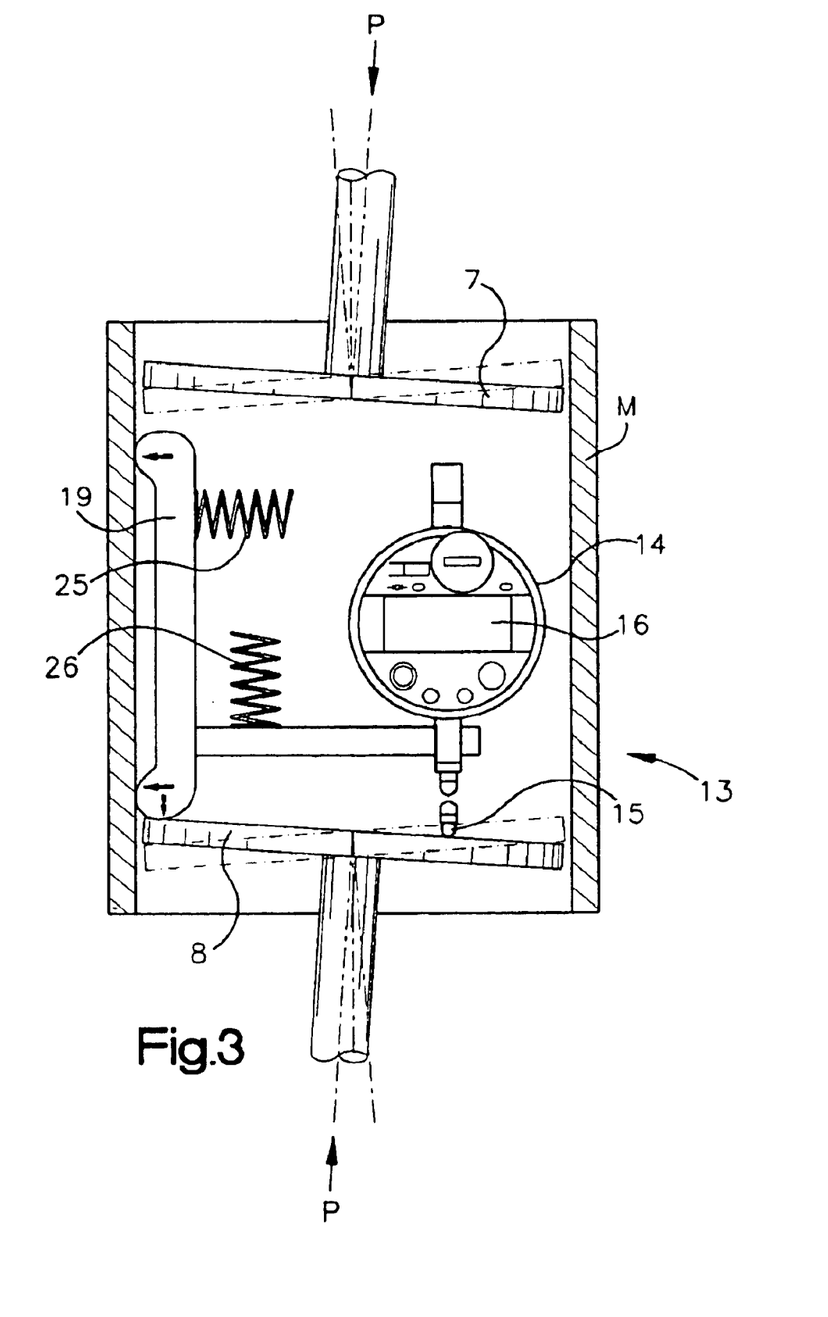
FIG. 3 illustrates a vertical cross-section of a specimen cylinder mold and a loading device in accordance with FIG. 1, with mechanical measuring elements of the angle of gyration built inside the loading device.

In order to be able to measure the angle of gyration of the gyratory compactor, the device in accordance with the invention may include measuring elements in order to measure the angle of gyration during the compaction test with the loading device. FIG. 3 illustrates a mechanical measuring element 13 for measuring the angle of gyration of a gyratory compactor in accordance with the invention which has been placed inside the body of the loading device 1 illustrated in FIG. 1 (in FIG. 3 the loading device only partly illustrated for clarity). The measuring element 13 includes a dial gauge 14 fixed to a separate frame 19 inside the loading device. The dial gauge has been adjusted by means of the frame 19 inside the loading device such that the measuring probe 15 reaches through a hole in a lower head surface of the loading device and contacts the bottom 8 of the specimen cylinder mold M at a certain point. This point is always located at the same distance from the vertical center line of the loading device 1. There is a horizontal spring 25 in the frame 19, which spring presses the frame through links placed transversal in the loading device frame (not illustrated in FIG. 3) against the inside wall of the specimen cylinder mold M, and a vertical spring 26, which presses the frame 19 through said links against the bottom 8 of the specimen cylinder mold M. When the angle of gyration of the gyratory compactor is induced, the position of the bottom 8 changes in respect with the cylinder inside wall and the measuring probe 15 moves and the readings of the dial gauge change. The frame 19 remains, however, all the time pressed by the horizontal spring 25 and the vertical spring 26 against the wall and the bottom 8 of the specimen cylinder mold M in accordance with the FIG. 3, although the loading device may move slightly while using the gyratory compactor. Therefore the dial gauge 14 fixed to the frame 19 measures the angle of gyration of the gyratory compactor exactly during the use of the gyratory compactor regardless of possible small clearances between the loading device and the specimen cylinder mold M.

In the application in accordance with the FIG. 3, the dial gauge 14 includes a transmitter 16 in order to transmit the results measured by the dial gauge outside the loading device and the gyratory compactor. The transmitter has a wireless contact with a measuring result processing unit (not illustrated in FIG. 3) placed near the gyratory compactor, such that the measuring results may be transmitted in real-time from the dial gauge to the measuring result processing unit. Alternatively the dial gauge may include an electronic memory unit, in which the measuring results may be saved, and from where the measuring results may be downloaded to the measuring result processing unit after measuring for later processing of the results. In this case the measuring result processing unit is a computer. In case the transmitting of the results from the transmitter is realized in real-time, a receiver is included in the computer in order to receive the results from the measuring sent by the transmitter in the dial gauge. If the transmitting of the results is realized after measuring by reading the results from the memory of the dial gauge, a suitable data collection card or corresponding installed in a free expansion slot of the computer is enough to receive the results. Furthermore, the computer operating as a measuring result processing unit includes a computer program, which saves the measuring results and defines the angle of gyration and the elastic deformations due to loads on the gyratory compactor due to the loading device as well as the correlation between the deformations and the magnitude of loading.

Figure 5:
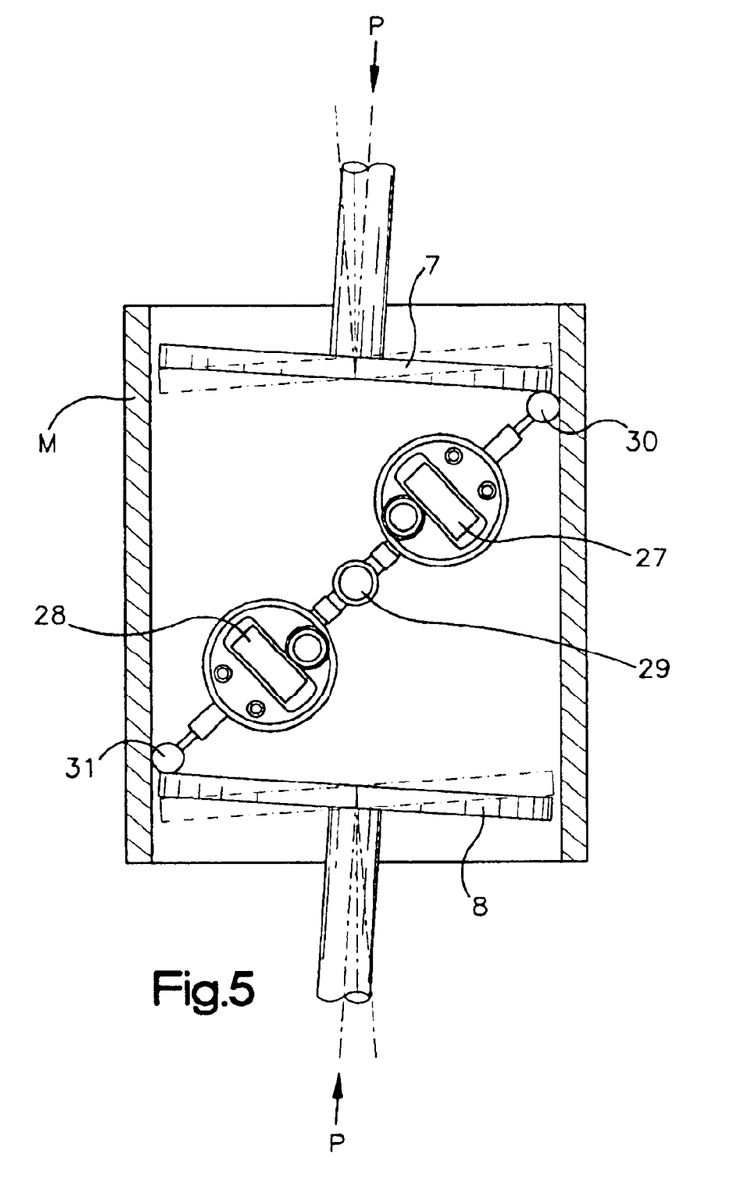
FIG. 5 illustrates a vertical cross-section of a specimen cylinder mold and a loading device in accordance with FIG. 1, with two mechanical measuring elements of the angle of gyration built inside the loading device.

The internal angle(s) of a mold in a gyratory compactor may alternatively be measured by one measuring procedure only, by using the diagonal length pick-up like in FIG. 5. This arrangement measures simultaneous the angle of gyration of cover (7) and of bottom (8) during the compaction test with the loading device 1. A bearing shaft (29) is placed in the center of the loading device and measuring dial gauges (27) and (28) are fixed by the shaft (29) to the loading device without clearance but easy to move. The spherical measuring probe (30) of the dial gauge (27) touches the cover (7) as well as the specimen cylinder wall and the spherical measuring probe (31) of the dial gauge (28) touches the bottom (8) as well as the specimen cylinder wall on the opposite side. When the angle of gyration is induced (the position of the cover (7) changes in respect with the cylinder inside wall) the measuring probe (30) moves and the readings of the dial gauge (27) changes. Simultaneous the position of the bottom (8) changes in respect with the cylinder inside wall, and the measuring probe (31) moves and the readings of the dial gauge (28) changes. Therefore, the dial gauge (27) measures the angle of gyration of the cover (7) and simultaneous the dial gauge (28) measures the angle of gyration of the bottom (8). A variation of this method is to measure without the bearing shaft (29), by one dial gauge only one length position diagonally. This way can measure directly the average internal angle, but this measurement will not give any information of possible differences of the cover (7) motion and bottom (8) motion.

While using the loading device in accordance with the FIGS. 1–3 and 5 the elastic deformations of the gyratory compactor are determined, for example, by the method steps as follows:

1. A loading device, illustrated in FIG. 1 is placed in the specimen cylinder mold of a gyratory compactor in the place of mass specimen, the loading of which loading device is earlier known while using the gyratory compactor.

2. Some measuring device/devices (for example a device in accordance with FIG. 3) measuring the angle of gyration during the use is mounted to the gyratory compactor.

3. The compactor is started and it starts to make a gyratory motion (by inducing an angle of gyration) and the direction of load due this movement circles such as in a normal compaction process of mass specimen.

4. Measuring results of the angle of gyration from the measuring elements are collected and saved to the memory of measuring result processing unit connected with the measuring elements in suitable intervals as long as the angles of gyration corresponding the different phases of the gyratory motion are defined in a functional way.

5. The device is stopped and the loading device is removed from the specimen cylinder mold.

6. An additional part/additional parts changing loads on gyratory compactor due to it is/are adjusted to the loading device (for example additional parts 17 and 18 in accordance with FIG. 2).

7. The loading device is again placed into the specimen cylinder mold and the compactor is started again.

8. The measuring results from the measuring element are collected and saved to the memory of the measuring result processing unit in accordance with paragraph 4.

9. The results are gathered and correlation between the angle of gyration and the load as well as other desired quality factors having influence on the compactor due to elastic deformations on the device are calculated.

These and other test method steps can be easily and rapidly performed and repeated in accordance with the invention due to the fact that the mold does not have to be charged or loaded with test specimen material such as soil or asphalt mix in combination with a testing device, emptied, cleaned and reloaded for repeated testing. This is highly advantageous to testing laboratories and commercial users who wish to perform multiple tests as quickly as possible and to obtain the most accurate measurement of internal gyration angle.

There must be noticed that stiffness of the frame and other parts of the gyratory compactor may be different depending the measuring radius direction. Determining this may need more sequences like determined above, by using different radial alignments of the measuring device by use of additional parts of different sizes. In the same way the stiffness of the cover and the bottom of the specimen cylinder mold may be different. These may be found out by turning the measuring probe side of the loading device to the corresponding plate and repeating the measuring sequence.

Figure 4:
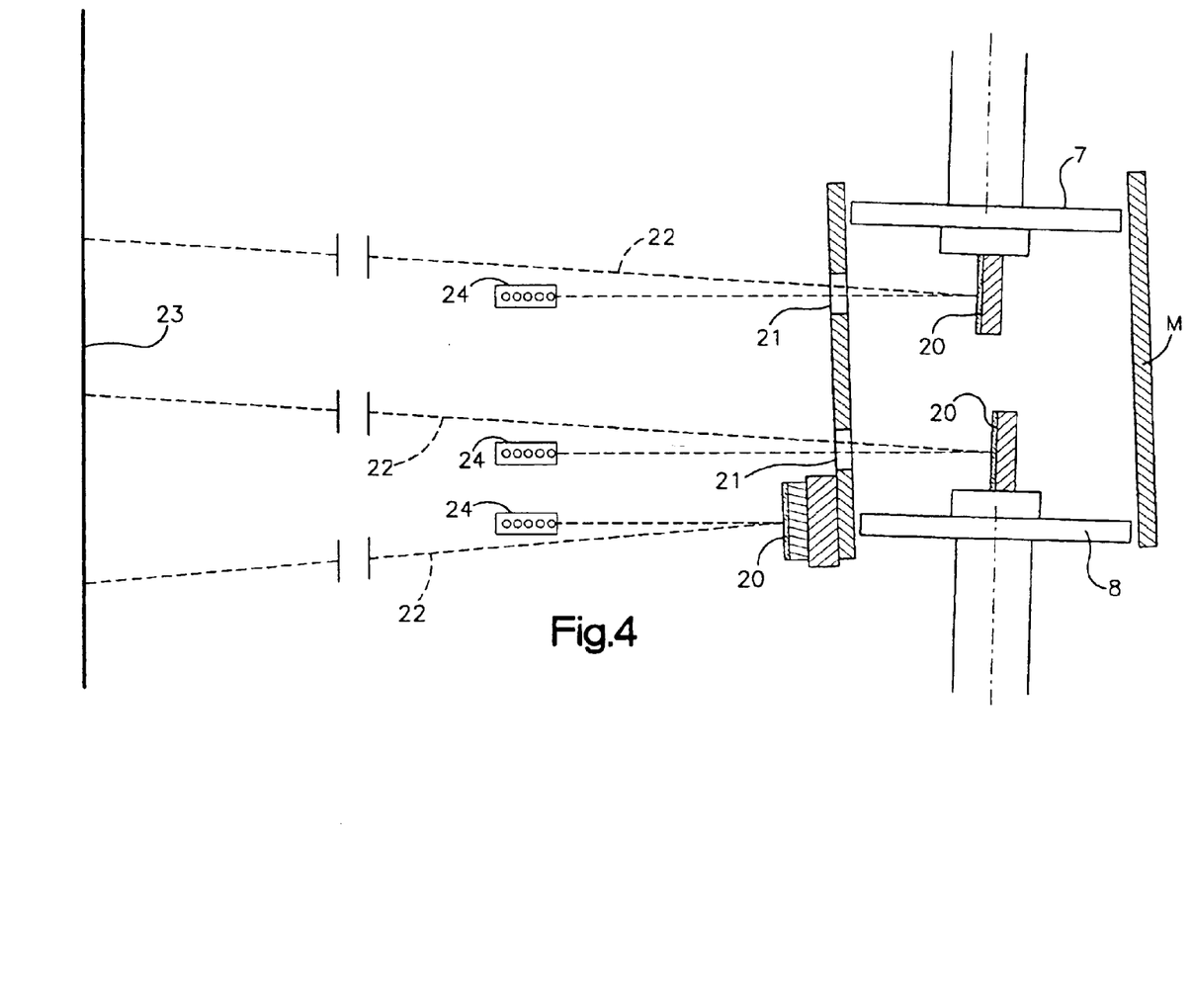
FIG. 4 illustrates a vertical cross-section of a specimen cylinder mold and a loading device in accordance with FIG. 1, with optical measuring elements of the angle of gyration.

Measurements may also be carried out outside the gyratory compactor, for example by adjusting devices sending and/or reflecting a directed light beam to the most important parts of the gyratory compactor. This kind of example is illustrated in FIG. 4 in a measuring arrangement in which there are mirrors 20 adjusted to the specimen cylinder mold M, the cover and the bottom of the gyratory compactor, by means of which the elastic deformations are optically defined. In the measuring solution in accordance with the FIG. 4 it is possible to examine the elastic deformations of construction due to the loading device from outside the specimen cylinder mold M, when there are holes 21 made to the wall and/or to some other suitable place wherefrom the light beams 22 send by the light sources 24 placed outside the gyratory compactor may be directed through mirrors 20 onto a surface for examining 23 placed in a rather far distance. This kind of measuring arrangement makes it easier to process the results and improves the accuracy of the measurement. The surface for examining 23 may be arranged, for example, on a suitable vertical surface, such as a paper on a wall where the light beams are reflected. While examining the results the reflecting points of the light beam from the gyratory compactor are marked on the paper with a pen. By measuring distances between the marked points the changes of the angle of gyration of the gyratory compactor due to loading are determined. While the distance between the surface for examining and the gyratory compactor is long enough (for example about 10 m) the deviations on the surface for examining due to elastic deformations are so great that they may be measured with a roll measure or a ruler and the obtained accuracy of measurement is very high.

The method in accordance with the invention may be realized in many different ways differing from the earlier explained application example. As a loading device causing the known loading whatever suitable object/mechanical appliance may be used, the loading of which on the gyratory compactor may be defined on beforehand the way explained above. For measuring the angle of gyration, measuring elements differing from what has earlier been presented may be used, such as various optical or mechanical devices measuring directly or indirectly the angle of gyration. One method to measure the angle of gyration is to adjust laser approximate sensors in a suitable place on the frame of a gyratory compactor, which measure the motions of the cover and the bottom in regard with the wall of the cylinder mold. Also other devices may be used as measuring devices such as those which are able to examine the motions and the changes in motion of the most important parts of a gyratory compactor as the gyratory compactor is in use. Furthermore, the measuring elements may be placed/adjusted in various places, such as outside the specimen cylinder mold on the frame of the device or to some other suitable place, where the angle of gyration or the earlier mentioned most important motions of the gyratory compactor and their changes may be measured during the use of the gyratory compactor. Furthermore, for example, the measuring result processing unit included in the device in accordance with the invention, with which the angle of gyration is defined from the results from the measuring elements as well as the correlation between loading and the elastic deformations are defined may be realized in many various ways differing from the earlier explained application example.

The invention is not limited to the presented advantageous application but it can vary within the frames of the idea of the invention formed in the claims.

What is claimed is:

1. A loading device for use in a specimen cylinder mold in a gyratory compactor, the loading device comprising:
    a cylindrical body with first and second head surfaces at opposite ends of the body, and a cylindrical casing surface between the first and second head surfaces, which fits with close clearance inside the specimen cylinder mold, each of the first and second head surfaces configured to have only a single contact point with a cover or bottom in the specimen cylinder mold, and
    a measuring element in the cylindrical body operative to measure an angle of gyration.

2. The loading device of claim 1 wherein the head surfaces extend or project from respective ends of the loading device body, and have a diameter less than a diameter of the loading device body.

3. The loading device of claim 1 wherein the head surfaces are chamfered.

4. The loading device of claim 1 wherein the head surfaces are integrally formed with the ends of the loading device.

5. The loading device of claim 1 wherein the head surfaces are detachable from the ends of the loading device.

6. The loading device of claim 1 wherein the head surfaces are configured to accept additional parts, the additional parts configured to have a single contact point with a cover or bottom of a specimen cylinder mold.

7. The loading device of claim 1 wherein the head surfaces are configured with hollows for receiving the additional parts.

8. The loading device of claim 1 wherein the head surfaces are in the form of cylinders which project from the respective ends of the loading device body and are co-axial with a center line axis of the loading device body.

9. The loading device of claim 1 wherein the measuring element comprises a gauge fixed to a frame, and a measuring probe which extends through one of the head surfaces.

10. The loading device of claim 1 further comprising a transmitter for transmitting data acquired by the measuring element from the loading device to an external receiver.

11. A loading device for applying a load and measuring an angle in a mold, the loading device comprising:
    a body having generally opposed head surfaces and a casing surface between the head surfaces, the casing surface dimensioned to fit with close clearance inside a mold;
    a measuring element within the body, the measuring element comprising a measuring probe located at a fixed distance from an axial center of the loading device body, the measuring probe extending through one of the head surfaces, the measuring probe connected to a spring-biased frame configured to contact a wall of a mold in which the loading device is located and to contact a mold cover or mold bottom located proximate to a head surface of the loading device body.

12. The loading device of claim 11 wherein the spring-biased frame has at least two contacts which extend through the loading device body at points between the head surfaces, and at least one contact which extends through a head surface of the loading device body.

13. The loading device of claim 11 wherein the measuring element further comprises a dial gauge attached to the frame.

14. The loading device of claim 11 wherein the frame of the measuring element is spring-biased toward a head surface and a casing surface of the loading device body.

15. The loading device of claim 11 further comprising a transmitter operatively coupled to the measuring element to transmit angle of gyration data measured by the measuring element.

* * * * *